(12) United States Patent
Lang

(10) Patent No.: US 6,516,620 B2
(45) Date of Patent: Feb. 11, 2003

(54) SPECIMEN HOLDER FOR WATER-CONTAINING PREPARATIONS AND METHOD FOR USING IT; AND HIGH-PRESSURE FREEZING DEVICE FOR THE SPECIMEN HOLDER

(75) Inventor: Anton Lang, Vienna (AT)

(73) Assignee: Leica Mikrosysteme GmbH, Wein (AT)

(*) Notice: Subject to any disclaimer, the term of this patent is extended or adjusted under 35 U.S.C. 154(b) by 0 days.

(21) Appl. No.: 09/821,749

(22) Filed: Mar. 30, 2001

(65) Prior Publication Data

US 2002/0059802 A1 May 23, 2002

(30) Foreign Application Priority Data

Mar. 30, 2000 (DE) .......................................... 100 15 773

(51) Int. Cl.[7] .............................................. F25D 17/02
(52) U.S. Cl. ............................................ 62/64; 62/373
(58) Field of Search ...................................... 62/64, 373

(56) References Cited

U.S. PATENT DOCUMENTS 4,107,937 A * 8/1978 Chmiel .......................... 62/64

FOREIGN PATENT DOCUMENTS

DE 1 806 741 6/1969
EP 0 853 238 7/1998

OTHER PUBLICATIONS

Leica EM HPF High–Pressure Freezer, pp. 1–4, 1994.

\* cited by examiner

Primary Examiner—Ronald Capossela
(74) Attorney, Agent, or Firm—Foley & Lardner

(57) ABSTRACT

A specimen holder for freezing water-containing preparations under high pressure is disclosed. The specimen holder possesses a housing sheath in which a cutout is provided. A specimen retention element is arranged in the cutout of the specimen holder, and can be sprayed with a coolant, from both sides, through the cutout. The specimen retention element is made up of at least a first part and a second part, a recess for holding the specimen is shaped in the second part. The second part is pressed with a screw against the first part in such a way that the recess is sealed in pressure-tight fashion. Also disclosed are a method and system for freezing water-bearing specimens under high pressure.

19 Claims, 3 Drawing Sheets

SPECIMEN HOLDER FOR WATER-CONTAINING PREPARATIONS AND METHOD FOR USING IT; AND HIGH-PRESSURE FREEZING DEVICE FOR THE SPECIMEN HOLDER

CROSS REFERENCE TO RELATED APPLICATIONS

This invention claims priority of a German patent application DE 100 15 773.4, filed Mar. 30, 2000, which is incorporated by reference herein.

FIELD OF THE INVENTION

The invention concerns a specimen holder for water-containing preparations. The invention furthermore concerns a method for using the specimen holder for water-containing preparations. In addition, the invention also concerns a high-pressure freezing device that uses a specimen holder for water-containing preparations.

BACKGROUND OF THE INVENTION

A method for rapid freezing of water-containing preparations under high pressure is known from DE Patent 1 806 741. The advantage of freezing water-containing preparations under high pressure can be explained as follows: If approximately 2000 bar of pressure is applied to the specimen during cooling, the cooling rate necessary for inducing vitrification (i.e., freezing with no formation of ice crystals) is reduced by a factor of 100. It is thus possible to vitrify specimens that are approximately 200 $\mu$m thick.

A first type of high-pressure freezing devices is represented by the Leica EM HPF and Balzers HPM 010 units. In devices of this type, liquid nitrogen is used as both the pressure transfer medium and the coolant. These high-pressure freezing devices have the disadvantage that they are comparatively large (approximately 0.8 m×1.6 m,×1.5 m) and weigh approximately 600 kg. The heavy construction means the price of such systems is high.

The freezing cycle in these systems proceeds as follows: In order to coordinate pressure buildup and cooling, the high-pressure chamber is first filled with ethanol. Cold liquid nitrogen is then fed into the pressure chamber by way of a high-pressure cylinder. The pressure chamber has an exhaust of substantially smaller dimensions than the dimensions of the supply line. Pressure in the chamber is built up by the restricted flow of pressurizing gas through the narrow exhaust. A disadvantageous effect in such systems is that a transition layer forms between the ethanol and the liquid nitrogen, which reduces the achievable cooling rate. The specimen, which is approximately 2 mm in diameter and 2000 $\mu$m thick, is located in two half-shells that are shaped in the pressure chamber.

The second type of high-pressure freezing device is represented by the Leica EM PACT unit. This high-pressure freezing device has separate circuits for pressure transfer and for cooling. This makes it possible to use relatively small equipment. A preparation holder that can withstand a pressure of 2000 bar is required, however. Pressure is built up in the preparation holder, and cooling is achieved by spraying a coolant, preferably liquid nitrogen, onto the exterior of the preparation holder. This requires a preparation holder with walls as thin as possible. One configuration of a possible preparation holder is known from EP 0 853 238 A1. The specimen is located in a tube with an inside diameter of approximately 0.3 mm. This small inside diameter has proven disadvantageous for many applications, since it can be particularly difficult to introduce the small and dimensionally unstable preparations into the tube. For many preparations (e.g. botanical preparations such as leaves or membranes) disk-shaped flakes are preferred, and as mentioned, these are difficult to introduce into the tube.

SUMMARY OF THE INVENTION

It is an object of the invention to create a specimen holder for water-containing specimens which is suitable for freezing planar specimen items under high pressure and which, in that context, makes possible easy handling of the specimen items. Attaining a high cooling rate is also intended.

This object is achieved by a specimen holder which is characterized in that a specimen retention element is arranged in the cutout of the specimen holder. The specimen retention element comprises at least a first part and a second part, a recess for specimen reception being shaped in the second part. The first and the second parts are joined to one another in such a way that the recess is sealed in pressure-tight fashion.

A further object of the invention is to create a method with which planar specimen items can be frozen under high pressure, thereby achieving efficient utilization of the coolant. The method is also intended to make possible easy handling of planar specimen items.

This is achieved, according to the present invention, by a method characterized by the following steps:

placing a specimen into the recess in the second part of the specimen retention element; and pressing the second part of the specimen retention element against the first part of the specimen retention element by way of a screw that acts on the second part.

Lastly, it is an object of the invention to create a high-pressure freezing device which uses the specimen holder according to the present invention.

This is achieved, according to the present invention, by a high-pressure freezing device for using a specimen holder for water-containing specimens which is characterized in that the specimen holder possesses a housing sheath in which a cutout is defined, and a specimen retention element is arranged in the cutout of the specimen holder;

the high-pressure freezing device defines a housing;

a first and a second nozzle are arranged with respect to the cutout in such a way that they lie directly opposite one another and thus direct coolant onto the specimen retention element from both sides; and that a high-pressure coupling connects to the specimen holder independent of the first and the second nozzle.

The advantage of the invention is that the specimen holder for water-containing specimens can be connected to a system for pressure generation in order to build up pressure within the specimen holder. Cooling is accomplished by spraying a coolant from outside onto the specimen holder, in particular in the region in which the water-containing specimen is introduced into a specimen retention element. It is particularly advantageous that the specimen retention element can be split, so as thereby to be able to receive preferably flat preparations. Shaped into a second part is a recess into which the specimen items can easily be placed. In addition, the first part and the second part are each configured in such a way that they have a contact surface which forms a thermal separation between the two parts and the housing sheath.

BRIEF DESCRIPTION OF THE DRAWINGS

The subject matter of the invention is schematically depicted in the drawings and will be described below with reference to the Figures, in which.

DETAILED DESCRIPTION OF THE INVENTION

Figure 1:
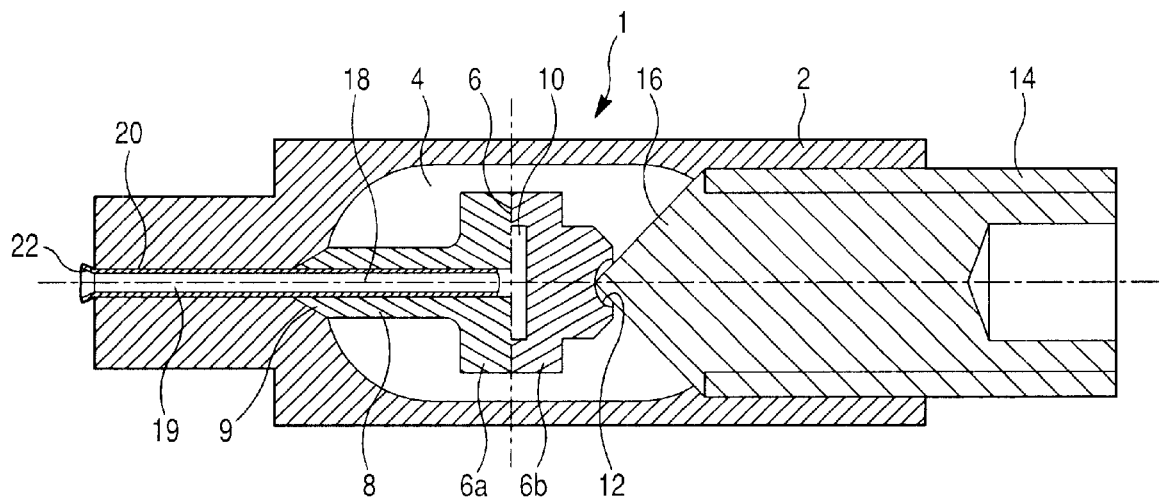
FIG. 1 shows a schematic side view of the specimen holder.

A side view of an embodiment of specimen holder 1 is depicted in FIG. 1. Specimen holder 1 must be configured in such a way that it exhibits pressure resistance greater than 2000 bar. Specimen holder 1 should have the lowest possible mass and the greatest possible thermal conductivity in order to allow high cooling rates.

In this embodiment, specimen holder 1 comprises a housing sheath 2 that is equipped with a cutout 4. A specimen retention element 6 is placed in cutout 4. Specimen retention element 6 comprises a first part 6a and a second part 6b. During cooling, the coolant, preferably liquid nitrogen, is sprayed onto specimen retention element 6 in cutout 4 from both sides, onto first and second parts 6a and 6b.

First part 6a of specimen retention element 6 possesses a constriction 8, i.e., a portion of first part 6a with a reduced cross section, at which first part 6a lies against housing sheath 2 of specimen holder 1. Constriction 8 of first part 6a furthermore has, on the side facing toward housing sheath 2, a protrusion 9 at which first part 6a lies directly against housing sheath 2. Second part 6b is provided opposite first part 6a. Configured in second part 6b, on the side located opposite first part 6a, is a recess 10 that is suitable for receiving the specimen items. Recess 10 is preferably disk-shaped, in order to be able to receive correspondingly shaped specimen items. Opposite recess 10, second part 6b possesses a depression 12 that is preferably configured in the form of a half-sphere.

A screw 14 is also arranged in housing sheath 2 of specimen holder 1, in such a way that it acts on second part 6b of specimen retention element 6. Screw 14 possesses a conical tip 16 at the end located opposite depression 12 of second part 6b. As screw 14 is screwed in, conical tip 16 engages into depression 12 of second part 6b. Screw 14 presses second part 6b against first part 6a. The two parts 6a and 6b have directly opposing surfaces which are configured such that the surfaces, fitted to and pressed against one another, seal off recess 10 from the outside in pressure-tight fashion. As already mentioned above, first part 6a possesses protrusion 9 which directly contacts housing sheath 2; and second part 6b possesses depression 12 which is connected via the screw to housing sheath 2. It is clearly evident from FIG. 1 that the result of this is a small contact surface between housing sheath 2 and first part 6a and second part 6b, respectively. This arrangement minimizes thermal conduction between the specimen retention element 6 and the housing sheath 2, thereby resulting in a thermal separation, which yields a savings in coolant during cooling. In addition, rapid heating after cooling is prevented.

First part 6a is equipped with a bore 18 that aligns with a corresponding bore 19 in housing sheath 2. Bore 18 in the first part ends at the surface of first part 6a which lies opposite recess 10 for specimen reception. A tube 20 is guided in bores 18 and 19 and, in the present embodiment, adhesively bonded in pressure-tight fashion to bore 18 in first part 6a and bore 19 in housing 2. Tube 20 possesses an end 22 that projects out of housing sheath 2. End 22 is shaped conically so that a high-pressure coupling (see FIG. 4) can be connected there.

The method for using specimen holder 1 comprises the following steps. Before the specimen is put in place, the specimen must be correctly cut to a specific shape. The specimen piece (or cut piece) is placed into recess 10 of second part 6b. Second part 6b is then placed against first part 6a. Screw 14 is screwed in, and depression 12 and conical end 16 of screw 14 thereby contact, causing second part 6b to be pressed against first part 6a. The housing sheath 2, together with the specimen located between the first and second parts 6a and 6b, is then inserted into the high-pressure freezing device. In this context, end 22 of tube 20 projecting out of housing sheath 2 is correspondingly connected to a high-pressure coupling.

The coolant (liquid nitrogen) is then sprayed in the region of cutout 4 of housing sheath 2. The small contact surfaces between second part 6b and screw 14, and between first part 6a and housing sheath 2, act thermally separate the specimen retention element 6 from the housing sheath 2 and screw 14. During cooling, as already mentioned above, the two parts 6a and 6b are entirely bathed in coolant, so that they cool down substantially more quickly than housing sheath 2. A considerable amount of liquid nitrogen for cooling is thereby saved, since a smaller mass needs to be cooled. Once cooling under pressure is complete, the low temperature is maintained and specimen holder 1 is opened with screw 14, and the preparation is removed along with part 6b. For subsequent specimen preparation, for example cryosubstitution, it is advisable to leave the specimen in second part 6b acting as a support, in order to simplify handling.

Figure 2:
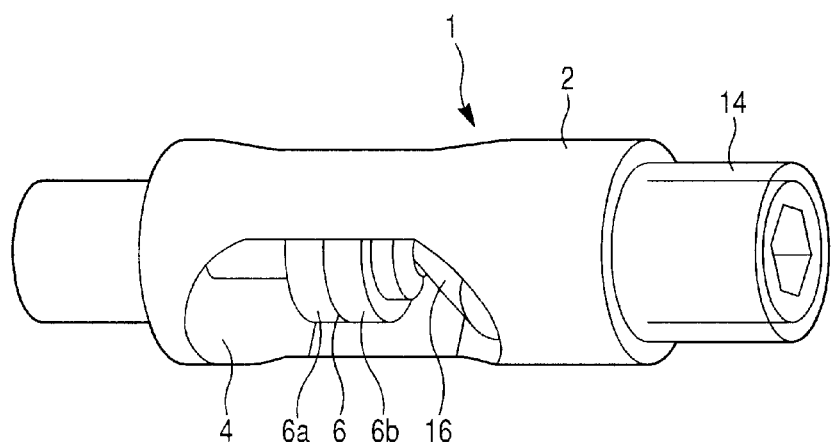
FIG. 2 shows a three-dimensional view of the specimen holder.

A perspective view of specimen holder 1 is depicted in FIG. 2. Specimen holder 1 is of substantially cylindrical configuration. Cutout 4 in housing sheath affords a view of first part 6a and second part 6b of specimen retention element 6. Cutout 4 is arranged in such a way that first and second parts 6a and 6b of specimen retention element 6 are freely accessible from both sides of specimen holder 1. Also evident is conical tip 16 of screw 14 which presses second part 6b against first part 6a.

Figure 3:
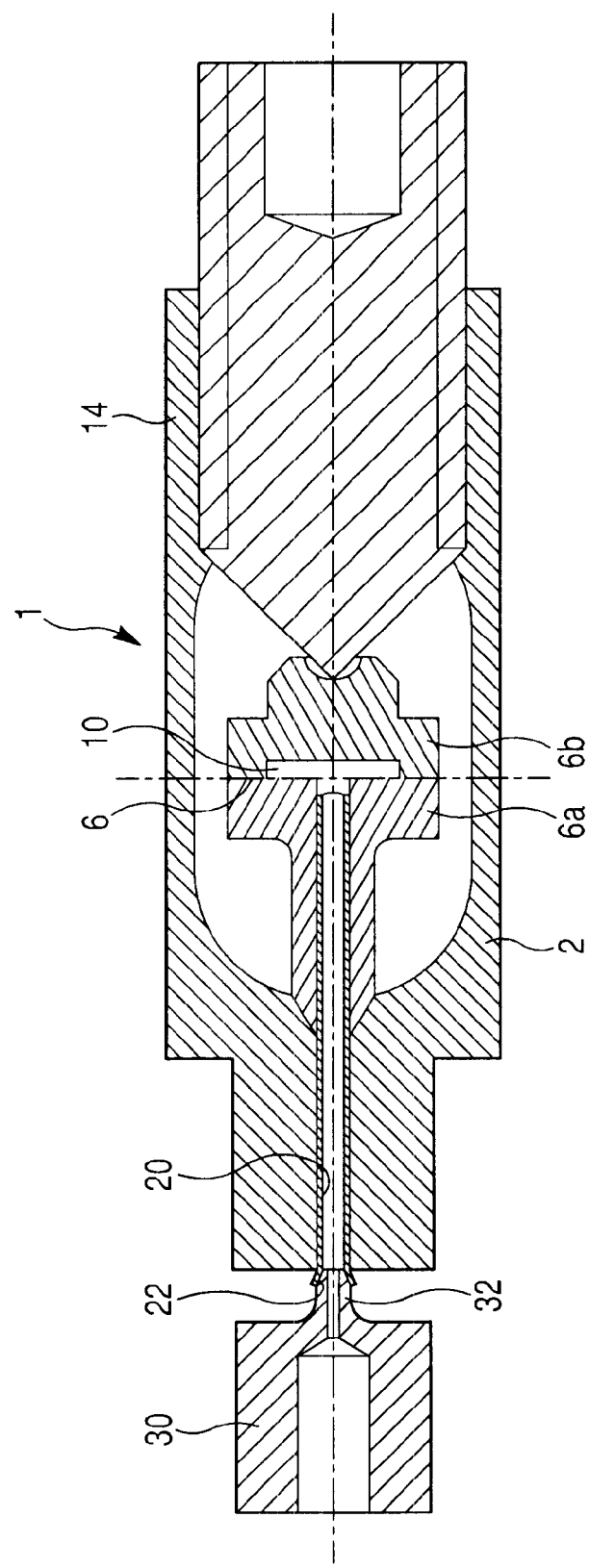
FIG. 3 shows a schematic side view of the specimen holder with the high-pressure coupling attached.

FIG. 3 shows a cross section through specimen holder 1 with a high-pressure coupling 30 attached. High-pressure coupling 30 has shaped onto it a connector piece 32 that fits conformingly with end 22 of tube 20. The connector piece 32 transfers the pressure provided by the high-pressure coupling 30 via tube 20 to recess 10 of second part 6b of the specimen retention element 6. Screw 14, screwed into housing 2, secures second part 6b against the high pressure and, because it is screwed in, ensures that recess 10 is sealed off in pressure-tight fashion from the outside.

Figure 4:
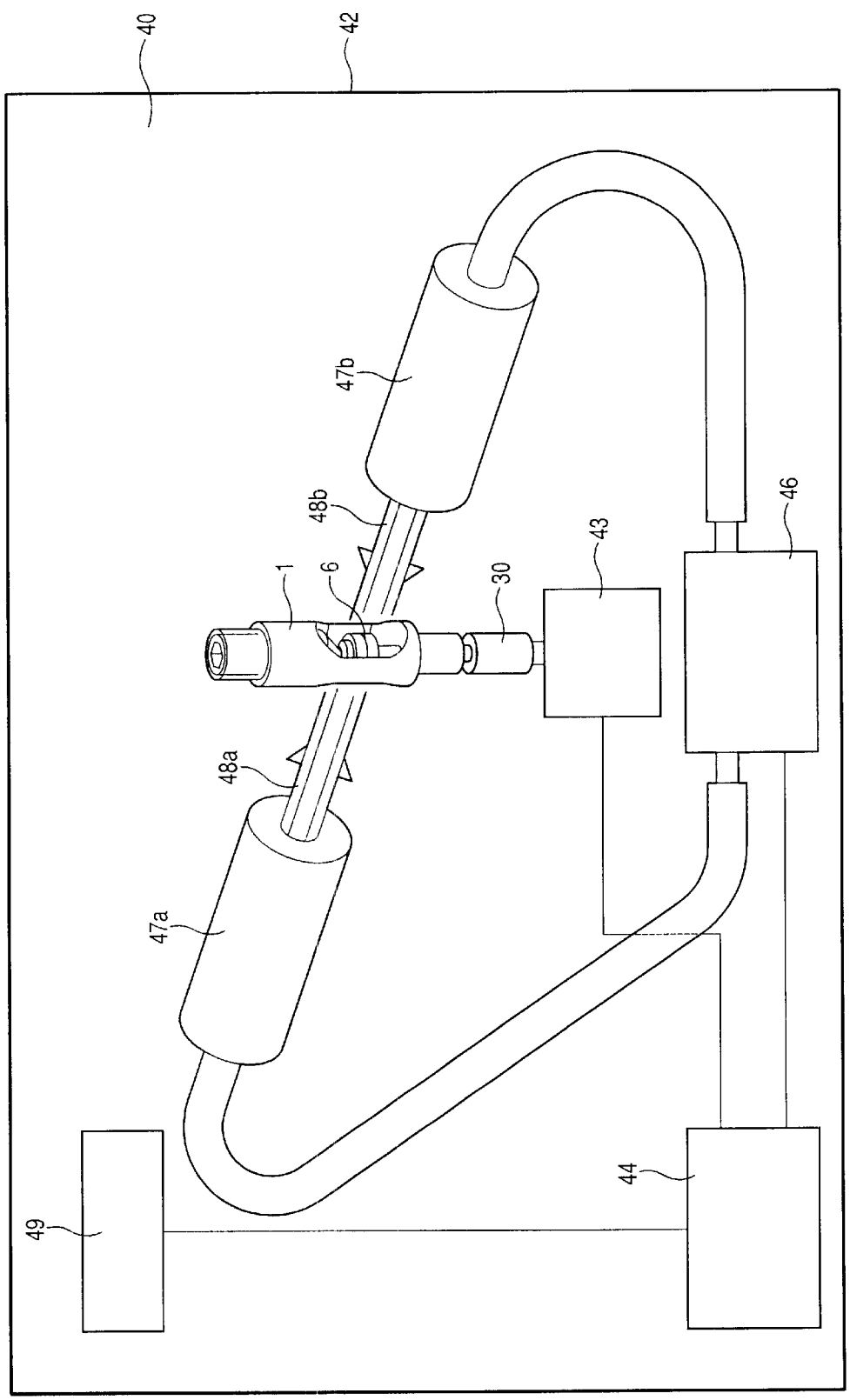
FIG. 4 schematically depicts the high-pressure freezing device with the specimen holder according to the present invention.

A schematic overall view of a high-pressure freezing device 40 that uses specimen holder 1 according to the present invention is depicted in FIG. 4. High-pressure freezing device 40 comprises a housing 42. An electronics unit 44, which processes user inputs and converts them into corresponding control signals, is provided in housing 42. Electronics unit 44 is connected to high-pressure generator 43 to ensure that the desired pressure acts on the specimen in recess 10. High-pressure coupling 30 couples the pressure from high-pressure generator 43 into specimen holder 1. Electronics unit 44 is also connected to a coolant reservoir 46 in order to maintain or interrupt the delivery of coolant into the region of specimen retention element 6. An interruption in coolant delivery is necessary when specimen retention element 6 has been cooled to the desired temperature. Liquid nitrogen is used as the coolant. The coolant is introduced into the region of specimen retention element 6 by way of a first and a second nozzle 47a and 47b. In the present embodiment, the coolant is sprayed out from the first and second nozzles 47a and 47b onto specimen retention element 6. The path traveled by the coolant from the first and second nozzles 47a and 47b onto specimen retention element 6 is depicted by arrows 48a and 48b. Also provided, on the exterior of the housing, is an input unit 49 with which a user can easily start the cooling operation or modify parameters.

The invention has been described with reference to one embodiment, but it is apparent that one skilled in the art can make modifications without thereby leaving the range of protection of the claims recited hereinafter.

PARTS LIST

1 Specimen holder
2 Housing sheath
4 Cutout
6 Specimen retention element
6a First part
6b Second part
8 Constriction
9 Protrusion
10 Recess
12 Depression
14 Screw
16 Conical tip
18 Bore
19 Bore
20 Tube
22 End
30 High-pressure coupling
32 Connector piece
40 High-pressure freezing device
42 Housing
43 High-pressure generator
44 Electronics unit
46 Coolant reservoir
47a First nozzle
47b Second nozzle
48a Arrow
48b Arrow
49 Input unit

What is claimed is:

1. A specimen holder, comprising:
   a housing sheath in which a cutout is provided; and
   a specimen retention element arranged in the cutout of the specimen holder, the specimen retention element comprising
      a first part, and
      a second part, the second part including a recess for specimen reception,
   wherein the first part and the second part are joined to one another such that the recess is sealed in pressure-tight fashion.

2. The specimen holder as defined in claim 1, wherein the recess for specimen reception is configured such that disk-shaped specimens with a thickness of 1 mm can be placed therein.

3. The specimen holder as defined in claim 1, wherein the first part and the second part each contact the housing sheath at a contact surface which is configured such that a thermal separation is formed between the housing sheath and the first part and the second part.

4. The specimen holder as defined in claim 3, wherein the first part has a constriction with a conical end at which the first part contacts the housing sheath.

5. The specimen holder as defined in claim 3, further comprising a screw threaded into the housing sheath, the screw having a conical end, and
   wherein the second part has a depression shaped at an end of the second part, and the conical end of the screw acts on the second part in the depression.

6. The specimen holder as defined in claim 5, wherein the screw is guided in the housing sheath such that the conical end of the screw engages the depression at the end of the second part in an approximately point-like contact.

7. The specimen holder as defined in claim 1, wherein the housing sheath has a bore, and the first part has a bore which aligns with the bore in the housing sheath; and further comprising a tube positioned within the bore in the housing sheath and within the bore in the first part, wherein the tube has two opposite ends, one end of the tube is positioned opposite the recess in the second part, and the other end of the tube is capable of being connected to a high-pressure coupling.

8. A method for using a specimen holder for water-containing preparations, the specimen holder comprising a housing sheath in which a cutout is provided, and a specimen retention element capable of being positioned with in the cutout of the specimen holder; the specimen retention element comprising a first part and a second part, the second part having a recess for specimen reception, and wherein the first part and the second part are pressed together such that the recess is sealed in pressure-tight fashion, comprising the steps:
   placing a specimen into the recess in the second part of the specimen retention element; and
   pressing the second part of the specimen retention element against the first part of the specimen retention element with a screw that acts on the second part.

9. The method as defined in claim 8, wherein the recess for specimen reception is configured such that disk-shaped specimens with a thickness of 1 mm can be placed therein.

10. The method as defined in claim 8, wherein the first part has a bore which aligns with a corresponding bore in the housing sheath, and the specimen holder further comprises a tube positioned within the bore in the first part and the bore in the housing sheath, wherein the tube has two opposite ends, one end of the tube is positioned opposite the recess in the second part, and the other end of the tube is connected to a high-pressure coupling.

11. The method as defined in claim 8, wherein a thermal separation is created at a point of contact between the first part and the housing sheath and at a point of contact between the second part and the housing sheath.

12. The method as defined in claim 8, further comprising a step of spraying a coolant through a first and second nozzle through the cutout onto the specimen retention element from two sides.

13. A high-pressure freezing system for freezing water-containing specimens, comprising:
   a housing;
   a specimen holder positioned within the housing, the specimen holder comprising a housing sheath in which a cutout is provided, and a specimen retention element (positioned in the cutout of the housing sheath;

a first nozzle and a second nozzle positioned within the housing and arranged with respect to the cutout such that the first nozzle and a second nozzle lie opposite one another so as to direct coolant onto the specimen retention element from two sides; and a high-pressure coupling coupled to the specimen retention element.

14. The high-pressure freezing system as defined in claim 13, further comprising:

a coolant reservoir positioned within the housing and fluidically coupled to the first nozzle and the second nozzle;

a high-pressure generator positioned within the housing and fluidically connected to the high-pressure coupling; and an electronics unit electronically coupled to the coolant reservoir and the high-pressure generator.

15. The high-pressure freezing system as defined in claim 14, further comprising an input unit electronically coupled to the electronics unit for use by an operator to enter parameters and start the freezing operation.

16. The high-pressure freezing system as defined in claim 13, wherein the specimen retention element comprises a first part and a second part, the second part has therein a recess for specimen reception, and the first part and the second part are pressed together such that the recess is sealed in pressure-tight fashion.

17. The high-pressure freezing system as defined in claim 16, wherein the second part of the specimen retention element is capable of being pressed by a screw against the first part of the specimen retention element.

18. The high-pressure freezing system as defined in claim 16, wherein the housing sheath has a bore, the first part of the specimen retention element has a bore which aligns with the bore in the housing sheath; and further comprising a tube positioned within the bore of the housing sheath and the bore of the first part, wherein the tube has two opposite ends, one end of the tube is positioned opposite the recess in the second part, and the other end of the tube is connected to the high-pressure coupling.

19. A high pressure freezing system, comprising:

a means for pressurizing;

a specimen holder means for holding a specimen to be frozen, the specimen holder means comprising a holder means for holding the specimen within a volume, a cover means for sealing the volume and connecting the volume to the means for pressurizing, and a housing means for pressing together the holder means and the cover means, the housing means being configured such that the holder means is thermally separated from the housing means; and a nozzle means for directing coolant onto the specimen holder means.

* * * * *